(12) United States Patent
Salamone et al.

(10) Patent No.: US 12,090,205 B2
(45) Date of Patent: Sep. 17, 2024

(54) POLOXAMER COMPOSITIONS WITH REDUCED SOL-GEL TRANSITION TEMPERATURES AND METHODS OF REDUCING THE SOL-GEL TRANSITION TEMPERATURE OF POLOXAMER COMPOSITIONS

(71) Applicant: ROCHAL TECHNOLOGIES LLC, Fort Worth, TX (US)

(72) Inventors: Joseph C. Salamone, San Antonio, TX (US); Rebecca Erin McMahon, San Antonio, TX (US); Suprena Emanuella Zariah Poleon, Fort Worth, TX (US); Ann Beal Salamone, San Antonio, TX (US)

(73) Assignee: ROCHAL TECHNOLOGIES LLC, Fort Worth, TX (US)

( * ) Notice: Subject to any disclaimer, the term of this patent is extended or adjusted under 35 U.S.C. 154(b) by 591 days.

(21) Appl. No.: 16/665,236

(22) Filed: Oct. 28, 2019

(65) Prior Publication Data

US 2021/0121575 A1     Apr. 29, 2021

(51) Int. Cl.
| | |
|---|---|
| *A61K 33/38* | (2006.01) |
| *A61K 9/06* | (2006.01) |
| *A61K 31/12* | (2006.01) |
| *A61K 31/137* | (2006.01) |
| *A61K 31/167* | (2006.01) |
| *A61K 31/4174* | (2006.01) |
| *A61K 31/616* | (2006.01) |
| *A61K 31/635* | (2006.01) |
| *A61K 31/785* | (2006.01) |
| *A61K 33/30* | (2006.01) |
| *A61K 35/64* | (2015.01) |
| *A61K 38/47* | (2006.01) |
| *A61K 47/10* | (2017.01) |
| *A61K 47/14* | (2017.01) |
| *A61K 47/34* | (2017.01) |

(52) U.S. Cl.
CPC ............... *A61K 47/34* (2013.01); *A61K 9/06* (2013.01); *A61K 31/12* (2013.01); *A61K 31/137* (2013.01); *A61K 31/167* (2013.01); *A61K 31/4174* (2013.01); *A61K 31/616* (2013.01); *A61K 31/635* (2013.01); *A61K 31/785* (2013.01); *A61K 33/30* (2013.01); *A61K 33/38* (2013.01); *A61K 35/64* (2013.01); *A61K 38/47* (2013.01); *A61K 47/10* (2013.01); *A61K 47/14* (2013.01); *C12Y 302/01* (2013.01)

(58) Field of Classification Search
CPC ............................... A61K 47/10; A61K 47/44
See application file for complete search history.

(56) References Cited

U.S. PATENT DOCUMENTS

| | | | |
|---|---|---|---|
| 4,188,373 A | 2/1980 | Krezanoski | |
| 5,858,937 A | 1/1999 | Richard et al. | |
| 6,482,435 B1 | 11/2002 | Stratton et al. | |
| 7,879,320 B2 | 2/2011 | Del Curto et al. | |
| 8,829,053 B2 * | 9/2014 | Salamone | A61P 31/04 514/738 |
| 2009/0017120 A1 | 1/2009 | Trimble et al. | |
| 2012/0277199 A1 | 11/2012 | Ye et al. | |
| 2013/0150451 A1 * | 6/2013 | Salamone | A01N 47/44 514/635 |
| 2015/0071864 A1 | 3/2015 | Lu et al. | |
| 2016/0144038 A1 | 5/2016 | Lu et al. | |

FOREIGN PATENT DOCUMENTS

| | | |
|---|---|---|
| EP | 1982696 | 10/2008 |
| WO | 2011049958 | 4/2011 |
| WO | 2014027006 | 2/2014 |

OTHER PUBLICATIONS

Jaya Raj Kumar et al (J Biomed Sci and Res, 2010, vol. 2, pp. 100-109) (Year: 2010).*
Miller, S.C., et al., "Rheological properties of poloxamer vehicles," International Journal of Pharmaceutics, 1984, vol. 18, pp. 269-276.
Dewan, M., et al., "Effect of methyl cellulose on gelation behavior and drug release from poloxamer based opthalmic formulations," International Journal of Biological Macromolecules, 2015, vol. 72, pp. 706-710.

* cited by examiner

*Primary Examiner* — Mark V Stevens
(74) *Attorney, Agent, or Firm* — DUANE MORRIS LLP; Gregory M. Lefkowitz; Brandon A. Chan

(57) ABSTRACT

The reduction in the sol-gel temperature of aqueous poloxamer surfactant compositions by the addition of hydrophobic vicinal diols is provided. Lowering of the sol-gel temperature and the gelling efficiency of water-soluble poloxamer block copolymers of polyethylene oxide-b-polypropylene oxide-b-polyethylene oxide has been markedly improved by the addition of small amounts of at least one hydrophobic vicinal diol, such as monoalkyl glycols, monoalkyl glycerols, or monoacyl glycerols. The decrease in the sol-gel temperature facilitates gel formation, and such gels exhibit greater residence time on a surface, particularly those with biological properties.

18 Claims, 3 Drawing Sheets

POLOXAMER COMPOSITIONS WITH REDUCED SOL-GEL TRANSITION TEMPERATURES AND METHODS OF REDUCING THE SOL-GEL TRANSITION TEMPERATURE OF POLOXAMER COMPOSITIONS

FIELD OF INVENTION

This disclosure relates generally to the reduction in the sol-gel temperature of aqueous poloxamer surfactant compositions by the addition of hydrophobic vicinal diols. The hydrophobic vicinal diols comprise monoalkyl glycols, monoalkyl glycerols, and monoacyl glycerols. The decrease in the sol-gel temperature facilitates a higher composition viscosity, wherein such higher viscosities allow greater residence time on a surface, particularly those of biological origin.

BACKGROUND OF THE INVENTION

Poloxamers are triblock copolymers of poly(ethylene oxide) and poly(propylene oxide) that have thermoreversible properties wherein they transform from a liquid-like behavior to gel-like behavior above a certain temperature and certain percent composition in aqueous systems. This phenomenon is termed the sol-gel transition, most often represented by the sol-gel transition temperature, $T_{sol-gel}$. The sol-gel transition can also be varied by certain excipients. By varying the concentration of poloxamer and other excipients, hydrogels with sol-gel transition point close to body temperature can be achieved. This transition is reversible by lowering the temperature, poloxamer concentration, or by changing excipients.

The structure of the poloxamers are arranged usually as poly(ethylene oxide-co-propylene oxide-co-ethylene oxide) or the reverse, poly(propylene oxide-co-ethylene oxide-co-propylene oxide). Poloxamers generally appear as white, waxy, free-flowing surfactants. For water-soluble poloxamers, at low concentrations ($10^{-4}$-$10^{-5}$ wt. %) monomolecular micelles are formed, but higher concentrations result in multimolecular aggregates consisting of a hydrophobic central core with their hydrophilic poly(ethylene oxide) chains facing outward. At a given temperature, micellization occurs in dilute compositions in selected solvents above the critical micellar concentration. At higher concentrations, above a critical gel concentration, the micelles can order into a lattice.

Commonly used types of poloxamers include Poloxamer 188, (also called Pluronic® F-68), Poloxamer 237 (also called Pluronic® F-87), Poloxamer 338 (also called Pluronic® F-108) and Poloxamer 407 (also called Pluronic® F-127), which are freely soluble in water. The "F" designation refers to the flake form of the product. Poloxomer 407 (Pluronic® F-127) has a good solubilizing capacity, low toxicity and has been used for biomedical applications.

Poloxamer 407 has an HLB (hydrophile-lipophile) value of 22. In general, HLB numbers>10 have an affinity for water (hydrophilic) and number<10 have an affinity for oil (lipophilic). Aqueous compositions of Poloxamer 407 show thermoreversible properties, wherein they transform from liquid-like behavior to gel-like behavior above the sol-gel temperature. Above the sol-gel transition temperature the compositions behave more solid-like, whereas below the sol-gel temperature the compositions behave more liquid-like (fluid). The rheological flow behavior of poloxamer compositions can be either Newtonian (liquid-like) or non-Newtonian (gel-like) based on the temperature and concentration of polymer. Below the sol-gel transition temperature, poloxamer compositions exhibit Newtonian properties, whereas above the sol-gel transition point they exhibit non-Newtonian properties.

Apart from temperature, gelation is also dependent on the concentration of poloxamer in composition. Gel formation occurs when the concentration of poloxamer is above critical micellar concentration. Poloxamer compositions of 20-30 wt. % concentrations form clear liquids at cold temperatures of 4-5° C., but gel at room temperature (~22-25° C.). The gel can return to liquid by cooling.

The sol-gel transition temperature decreases with increase in the poloxamer concentration.

Excipients may also influence the sol-gel transition temperature of the poloxamers. For example, hydrochloric acid, propylene glycol and ethanol increase the sol-gel transition temperature, whereas sodium chloride, $Na_2HPO_4$ and sodium alginate, as well as an increase in pH and ionic strength, decrease the gel-sol transition temperature. The gel systems have primarily been used in topical biomaterials for the sustained release of active pharmaceutical agents. Sustained release of such drugs helps to maintain therapeutic drug concentrations over a longer period-of-time and helps to decrease dosage intervals, thereby increasing patient compliance.

There has been extensive research into poloxamers, which has resulted in various patent filings including, but not limited to U.S. Pat. Nos. 7,879,320, 4,188,373, 6,482,435, EP Publication No. 1982696, U.S. Patent Application Publication No. 2016/0144038, U.S. Patent Application Publication No. 2009/0017120, U.S. Patent Application Publication No. 2012/0277199, U.S. Patent Application Publication No. 2015/0071864, PCT Publication No. WO2014/027006, U.S. Pat. No. 8,829,053, and EP Patent Publication No. 2490722.

SUMMARY

In various embodiments, a method of lowering the sol-gel temperature of an aqueous poloxamer gel composition by up to 12° C. is provided. The method includes adding 0.1 to 1.8 wt. % hydrophobic vicinal diols to the aqueous poloxamer gel composition, wherein the hydrophobic vicinal diols are 6-carbon to 16-carbon length monoalkyl glycols, monoalkyl glycerols, monoacyl glycerols, or a combination thereof.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

DETAILED DESCRIPTION OF THE INVENTION

Figure 1:
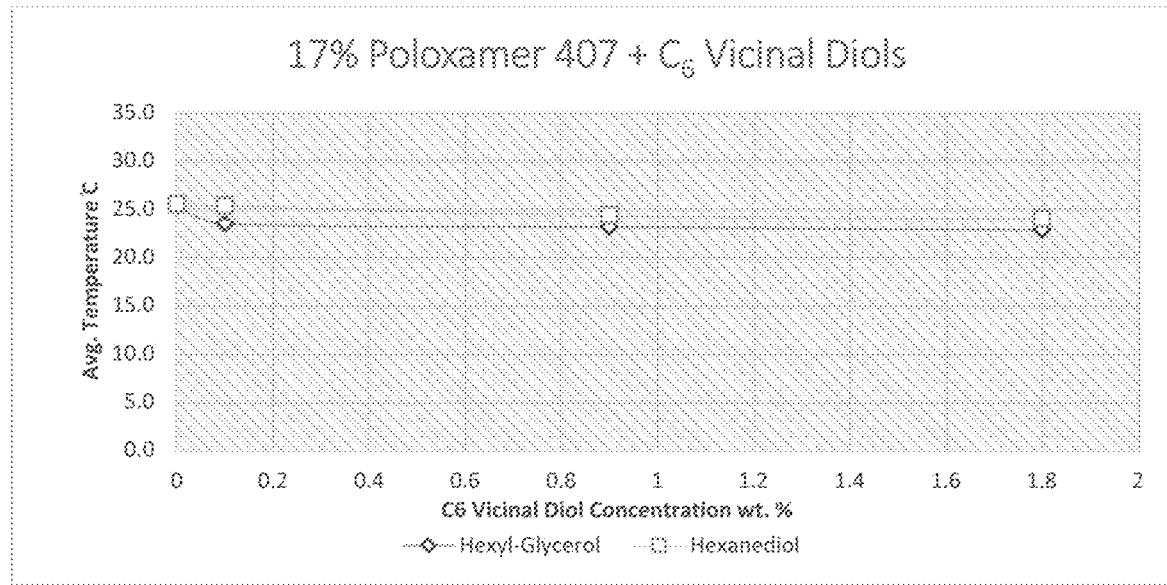
FIG. 1 is a graph showing the average sol-gel temperatures of Poloxamer 407 after the addition of six carbon (C6) chain monoalkyl glycols and monoalkyl glycerols at 0-1.8 wt. %.

Reference will now be made in detail to the present preferred embodiment(s), an examples of which is/are illustrated in the accompanying drawings.

This disclosure relates generally to the reduction in the sol-gel temperature of aqueous poloxamer surfactant compositions (which can be poloxamer gel solutions, poloxamer gel suspensions, poloxamer gel mixtures, etc.) by the addition of hydrophobic vicinal diols. It has been surprisingly discovered that the lowering of the sol-gel temperature and the gelling efficiency of water-soluble poloxamer block copolymers of polyethylene oxide-b-polypropylene oxide-b-polyethylene oxide has been markedly improved by the addition of small amounts of at least one hydrophobic vicinal diol. Examples of hydrophobic vicinal diols useful for use in the poloxamer gel compositions include monoalkyl glycols, monoalkyl glycerols, monoacyl glycerols, and combinations thereof. The decrease in the sol-gel temperature facilitates gel formation (e.g., on a biological surface), wherein such gels allow greater residence time on a surface in the applied environment, particularly those with biological properties. If an active ingredient, such as, a cosmetic agent, a biological agent, a pharmaceutical agent, a wound-healing agent, an enzymatic agent or an antimicrobial agent is added to such a system, the active agent will thus be in proximity of the biological surface for an extended period-of-time.

One of the problems associated with formulations applied topically to the body is their short duration of action, often caused by their limited residence time at the target site. A major problem in the delivery of active agents (e.g., wound-healing agents and drugs) to body cavities and body surfaces is thus maintaining the active agent at the intended site of action for a sufficient period of time to achieve targeted delivery of the active agent and, thus, highly effective treatment of the medical or cosmetic condition.

In some embodiments, a poloxamer gel composition comprising 0.05 to 5 wt. % hydrophobic vicinal diol component, and 10 to 65 wt. % of a poloxamer component is disclosed. The hydrophobic vicinal diol component is 6-carbon to 16-carbon length monoalkyl glycols, monoalkyl glycerols, monoacyl glycerols, or a combination thereof, and wherein the hydrophobic vicinal diol component depresses a sol-gel temperature of the aqueous poloxamer equivalent by at least 1.0° C.

In some embodiments, the hydrophobic vicinal diol component comprises at least 0.075 wt %, or at least 0.1 wt %, or at least 0.15 wt. %, or at least 2.0 wt. % of the poloxamer gel composition. In some embodiments, the hydrophobic vicinal diol component is less than 5 wt. %, or less than 4 wt. %, or less than 3.5 wt. %, or less than 3.0 wt. %, or less than 2.5 wt. %, or less than 2.0 wt. %, or less 1.8 wt. % of the poloxamer gel composition.

In some embodiments, the hydrophobic vicinal diol component is completely solubilized in the poloxamer gel composition. In some embodiments, the hydrophobic vicinal diol component is completely solubilized in the poloxamer gel composition without any non-poloxamer surfactants.

In some embodiments, the poloxamer component is selected from the group consisting of Poloxamer 108, Poloxamer 124, Poloxamer 188, Poloxamer 127, Poloxamer 237, Poloxamer 238, Poloxamer 288, Poloxamer 335, Poloxamer 338, Poloxamer 407, and combinations thereof.

In some embodiments, the composition is aqueous.

In some embodiments, the hydrophobic vicinal diol component depresses a sol-gel temperature of the aqueous poloxamer equivalent by at least 1.0° C. In some embodiments, the hydrophobic vicinal diol component depresses a sol-gel temperature of the aqueous poloxamer equivalent by by at least 1.5° C., at least 2.0° C., at least 2.5° C., at least 3.0° C., by at least 3.5° C., or at least 4.0° C., or at least 4.5° C., or at least 5.0° C. As used herein, the "aqueous poloxamer equivalent" refers to an aqueous composition consisting of only water and the specified percentage of poloxamer component without further components or ingredients.

In some embodiments, the sol-gel temperature of the aqueous poloxamer equivalent is at least 26.5° C. In some embodiments, the sol-gel temperature of the aqueous poloxamer equivalent is at least 27.0° C., or at least 27.5° C., or at least 28.0° C., or at least 28.5° C., or at least 29° C.

The vicinal diols useful in the poloxamer gel compositions described herein include hydrophobic monoalkyl glycols, monoalkyl glycerols, and monoacyl glycerols. Monoalkyl glycerols are also referred to as glycerol alkyl ethers, while monoacyl glycerols are also referred to as glycerol alkyl esters. The substituents on the monoalkyl glycol, the monoalkyl glycerol and the monoacyl glycerol are preferentially aliphatic, and can be linear or branched, and saturated or unsaturated and the two hydroxy groups are vicinal to one another.

Monoalkyl glycols useful in the poloxamer gel compositions described herein can have a structure represented by formula 1, as follows:

formula 1 wherein R=C6-C16 branched or unbranched alkyl group or alkylene group. In some embodiments, R=C6-C14 branched or unbranched alkyl group or alkylene group, or R=C8-C12 branched or unbranched alkyl group or alkylene group.

Monoalkyl glycerols (alternately referred to as a glycerol alkyl ether) useful in the poloxamer gel compositions described herein can have a structure represented by formula 2, as follows:

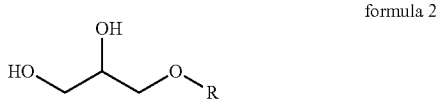

formula 2 wherein R=C6-C16 branched or unbranched alkyl group or alkylene group. In some embodiments, R=C6-C14 branched or unbranched alkyl group or alkylene group, or R=C8-C12 branched or unbranched alkyl group or alkylene group.

Monoacyl glycerols useful in the poloxamer gel compositions described herein can have a structure represented by formula 3 as follows:

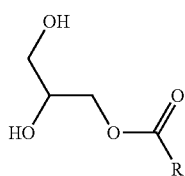

formula 3 wherein R=C6-C16 branched or unbranched alkyl group or alkylene group. In some embodiments, R=C6-C14 branched or unbranched alkyl group or alkylene group, or R=C8-C12 branched or unbranched alkyl group or alkylene group.

For each of the vicinal diols, when R is branched, the respective compound can exist as a racemic mixture of R,S components, as a pure enantiomer of R or S configuration, or as an enantiomer R,S enriched mixture.

Examples of specific monoalkyl glycols include, but are not limited to, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, and 1,2-hexadecanediol.

Examples of specific monoalkyl glycerols include, but are not limited to, glycerol 1-hexyl ether, glycerol 1-heptyl ether, glycerol 1-octyl ether, glycerol 1-(2-ethylhexyl)ether (also known as octoxyglycerin, 2-ethylhexyl glycerin, 3-(2-ethylhexyloxy)propane-1,2-diol, and Sensiva® SC 50), glycerol 1-nonyl ether, glycerol 1-decyl ether, glyceryl 1-undecyl ether, glycerol 1-dodecyl ether, glycerol 1-tridecyl ether, glycerol 1-tetradecyl ether, glycerol 1-pentadecyl ether, and glycerol 1-hexadecyl ether.

Examples of specific monoacyl glycerols include, but are not limited to, glycerol monohexanoate (2,3-dihydroxypropyl hexanoate), glycerol monoheptanoate (2,3-dihydroxypropyl hexanoate), glycerol monooctanoate (2,3-dihydroxypropyl octanoate, monocaprylin), glycerol mono nonanoate, glycerol monodecanoate (glycerol 1-decanoate), glycerol monoundecanoate (2,3-dihydroxypropyl undecanoate), glycerol monododecanoate (monolaurin, also called glycerol monolaurate and Lauricidin®), glycerol monotridecanoate, glycerol monotetradecanoate (monomyristin), glycerol monopentadecanoate, glycerol monohexadecanoate, glycerol monoheptadecanoate, glycerol monopentadecanoate, and glycerol monohexadecanoate.

In some embodiments, the vicinal diol is a combination of a monoalkyl glycol and a monoalkyl glycerol, In some embodiments, the vicinal diol is a combination of a monoalkyl glycol and a monoacyl glycerol. In some embodiments, the vicinal diol is a combination of a monoalkyl glycerol and a monoacyl glycerol. In some embodiments, the vicinal diol is a monoalkyl glycol, a monoalkyl glycerol, and a monoacyl glycerol.

Whereas the long chain vicinal diols may have poor solubility in water, the poloxamers act as compatibilizers (e.g., surfactants), so addition of high poloxamer concentrations facilitates the overall solubility of the vicinal diols in the compositions described herein.

As used herein, "poloxamers" refers to non-toxic, non-ionic triblock copolymers composed of a central hydrophobic chain of polyoxypropylene (polypropylene oxide) coupled by two hydrophilic chains of polyoxyethylene (poly (ethylene oxide)) in the alpha, omega positions. Because the lengths of the polymer blocks can be customized, many different poloxamers exist that have slightly different properties. For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g. P407=poloxamer with a polyoxypropylene molecular mass of 4000 g/mol and a 70% polyoxyethylene content). For the Pluronic and Synperonic tradenames, coding of these copolymers starts with a letter to define its physical form at room temperature (L=liquid, P=paste, F=flake (solid)) followed by two or three digits, The first digit (two digits in a three-digit number) in the numerical designation, multiplied by 300, indicates the approximate molecular weight of the hydrophobe; and the last digit×10 gives the percentage polyoxyethylene content (e.g., F-108 indicates a polyoxypropylene molecular mass of 3000 g/mol and a 80% polyoxyethylene content).

In some embodiments, the poloxamer surfactant, or surface-active agent, may be Poloxamer 108, Poloxamer 127, Poloxamer 188, Poloxamer 237, Poloxamer 238, Poloxamer 288, Poloxamer 335, Poloxamer 338, Poloxamer 407 or combinations thereof. In certain embodiments, the surfactant may be Poloxamer 338. In certain other embodiments, the surfactant may be Poloxamer 407. In water at room temperature (~24° C.), Poloxamer 338 (Pluronic® F-108) has been shown to gel at 30 wt. %, while Poloxamer 407 (Pluronic® F-127) gels at 20 wt. %.

Any of the compositions described herein can be aqueous compositions. As used herein, "aqueous" compositions refer to a spectrum of water-based compositions including, but not limited to, homogeneous solutions in water with solubilized components, emulsified compositions in water stabilized by surfactants or hydrophilic polymers, and viscous or gelled homogeneous or emulsified compositions in water.

If maintenance of the osmolarity is required, examples of suitable tonicity adjusting agents that can be included in the poloxamer gel compositions include, but are not limited to: sodium chloride and potassium chloride, glycerin, propylene glycol, mannitol and sorbitol. These agents are typically used individually in amounts ranging from about 0.01 to 2.5% (w/v) and preferably, from about 0.05 to about 1.5% (w/v). Preferably, the tonicity agent will be employed in an amount to provide a final osmotic value of from 10 to 320 mOsm/kg and more preferably between about 200 to about 300 mOsm/kg, and most preferably between about 260 to about 290 mOsm/Kg. Sodium chloride is most preferred to adjust the composition tonicity.

The pH of the poloxamer gel compositions is preferably adjusted to between 4.5 to 7.0. Suitable buffers to adjust pH can include sodium citrate, potassium citrate, citric acid, sodium dihydrogen phosphate, disodium monophosphate, boric acid, sodium borate, tartrate, phthalate, succinate, acetate, propionate, maleate salts, tris(hydroxymethyl)aminomethane, amino alcohol buffers, and Good buffers (such as ACES, PIPES, and MOPOSO), and mixtures thereof. One or more buffers can be added to compositions of the present disclosure in amounts ranging between approximately 0.01 to 2.0 weight percent by volume, but more preferably between approximately 0.05 to 0.5 weight percent by volume.

Emollients/moisturizers and humectants can be added to the poloxamer gel compositions to provide a soothing composition. Emollients/moisturizers function by forming an oily layer on the top of the skin that traps water in the skin. Petrolatum, lanolin, mineral oil, dimethicone, and siloxy compounds are common emollients. Other emollients include isopropyl palmitate, isopropyl myristate, isopropyl isostearate, isostearyl isostearate, diisopropyl sebacate, propylene dipelargonate, 2-ethylhexyl isononoate, 2-ethylhexyl stearate, cetyl lactate, lauryl lactate, isopropyl lanolate, 2-ethylhexyl salicylate, cetyl myristate, oleyl myristate, oleyl stearate, oleyl oleate, hexyl laurate, and isohexyl laurate, lanolin, olive oil, cocoa butter, shea butter, octyldodecanol, hexyldecanolc dicaprylylether and decyl oleate. Humectants include lecithin, and polyethylene glycol. Humectants function by drawing water into the outer layer of skin.

It is often desirable to include water-soluble viscosity builders in the poloxamer gel compositions of the present disclosure. Because of their demulcent effect and possible hydrophobic interactions with biological tissue, aiding the retention of the compositions on a surface, particularly of biological origin, water-soluble polymers can enhance the compositions interaction with a surface. Because of this behavior, such water-soluble polymers can increase the residence time of the composition on a surface.

Water-soluble polymers useful herein include, but are not limited to, aloe vera, methylcellulose, hydroxyethylcellulose, hydroxypropylcellulose, hydroxypropylmethylcellulose, carboxymethylcellulose, polyquaternium-1, polyquaternium-6, polyquaternium-10, guar, hydroxypropylguar, hydroxypropylmethylguar, cationic guar, carboxymethylguar, hydroxymethylchitosan, hydroxypropylchitosan, carboxymethylchitosan, N-[(2-hydroxy-3-trimethylammonium)propyl]chitosan chloride, water-soluble chitosan, hyaluronic acid and its salts, chondroitin sulfate, heparin, dermatan sulfate, amylose, amylopectin, pectin, locust bean gum, alginate, dextran, carrageenan, xanthan gum, gellan gum, scleroglucan, schizophyllan, gum arabic, gum ghatti, gum karaya, gum tragacanth, pectins, starch and its modifications, tamarind gum, poly(vinyl alcohol), poly(ethylene oxide), poly(ethylene glycol), poly(methyl vinyl ether), polyacrylamide, poly(N,N-dimethylacrylamide), poly(N-vinylacetamide), poly(N-vinylformamide), poly(2-hydroxyethyl methacrylate), poly(glyceryl methacrylate), poly(N-vinylpyrrolidone), poly(N,N-dimethylaminoethyl methacrylate), poly(N,N-dimethylaminopropyl acrylamide), polyvinylamine, poly(N-isopropylacrylamide) and poly(N-vinylcaprolactam), the latter two hydrated below their Lower Critical Solution Temperatures, and the like, and combinations thereof. Such water-soluble polymers may be employed in amounts ranging from about 0.01 to about 10.0 weight percent.

More preferred hydrophilic polymers comprise hydroxyethylcllulose, hydroxypropylmethylcellulose, hydroxypropylcellulose, hydroxypropylguar, hydroxymethylchitosan, poly(ethylene oxide), N-[(2-hydroxy-3-trimethylammonium)propyl]chitosan chloride, with hydroxyethylcellulose and hydroxymethylpropylcellulose being most preferred.

If chelating agents are required to sequester metal ions, such as found in matrix metalloproteases (MMPs), enzymes that can impede tissue formation and healing by breaking down collagen, or in removal of such metal ion deposits on structures, the chelating agent is selected from any compound that is able to sequester monovalent or polyvalent metal ions, such as preferentially including, calcium, magnesium, barium, cerium, cobalt, copper, iron, manganese, nickel, strontium or zinc, and is pharmaceutically or veterinary acceptable if used on biological tissue.

Suitable chelating agents comprise, but are not limited to, citric acid, citrate salts, aminocarboxylic acids, ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanetetraacetic acid, O,O'-bis(2-aminoethypethyleneglycoltetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, N,N-bis(2-hydroxyethyl)glycine, 1,3-diamino-2-hydroxypropanetetraacetic acid, 1,2-diaminopropanetetraacetic acid, ethylenediaminetetrakis(methylenephosphonic acid), N-(2-hydroxyethyl)iminodiacetic acid and biphosphonates such as etidronate, and salts thereof. Suitable chelating agents include for example but are not limited to hydroxyalkylphosphonates as disclosed in U.S. Pat. No. 5,858,937, specifically the tetrasodium salt of 1-hydroxyethylidene-1,1-diphosphonic acid, also referred to as tetrasodium etidronate, commercially available from Monsanto Company as DeQuest 2016 diphosphonic acid sodium salt or phosphonate.

Especially preferred chelating agents are mixed salts of EDTA such as disodium, trisodium, tetrasodium, dipotassium, tripotassium, tetrapotassium, lithium, dilithium, ammonium, diammonium, triammonium, tetraammonium, calcium and calcium-disodium, more preferably disodium, trisodium or tetrasodium salts of EDTA, and most preferably disodium EDTA and trisodium EDTA. The concentration of chelating agent can range from 0.01 weight % to 1.0 weight %, or from 0.025 to 0.5 weight %, or from 0.05 to 0.15 weight %.

In addition to a homogeneous solution, it is also possible for the poloxamer gel compositions to be an emulsion, a miniemulsion, a microemulsion or an inverse emulsion utilizing the poloxamer surfactant to solubilize an active agent that is normally water insoluble or difficult to solubilize. Organic and inorganic active agents that can be solubilized include, but are not limited to, antibiotics, silver salts and silver nanoparticles, zinc and zinc salts, magnesium salts, phosphorous compounds, iodine compounds, antibacterial agents, antifungal agents, antiviral agents, antiprotozoal agents, antimicrobials, analgesics, protease inhibitors, anti-allergenics, anti-inflammatories, vasoconstrictors, vasodilators, anticlotting agents, hormones, peptides, nucleic acids, saccharides, lipids, glycolipids, glycoproteins, endocrine hormones, growth hormones, growth factors, low molecular weight water-soluble collagen, collagen peptides, gelatin, heat shock proteins, immunological response modifiers, anti-cancer agents, cytokines, and mixtures thereof, as well as organic solvents that provide increased oxygen to ischemic wounds. Of significance are the addition of organic solvents, such as siloxanes and fluorocarbons, which increase oxygen solubility and transport. Of particular significance is the use of a volatile, non-burning, non-stinging, non-sensitizing, siloxane solvent of hexamethyldisiloxane (HMDS). The emulsion is prepared by slowly adding the HMDS to the composite composition up to the concentration wherein phase separation occurs between the organic solvent and the emulsified composition.

Essential oils can also be added to the poloxamer gel compositions as fragrance or aromatherapy agents, and/or as antimicrobial agents, including thymol, menthol, sandalwood, camphor, agathosma, cardamom, cinnamon, jasmine, lavender, frankincense, myrrh, geranium, juniper, menthol, pine, lemon, rose, eucalyptus, clove, orange, mint, linalool, spearmint, peppermint, lemongrass, bergamot, citronella, cypress, nutmeg, spruce, tea tree, wintergreen (methyl salicylate), vanilla, hemp essential oil, and the like.

In topical applications, the poloxamer gel compositions may be delivered in different forms. Exemplary forms include, but not limited to, liquids, creams, foams, lotions, gels and aerosols. These compositions can also be imbibed by swabs, cloth, sponges, foams, dressing materials and non-woven and paper products, such as paper towels and wipes.

As used herein, "hydrophobic" refers to repelling water, being insoluble or relatively insoluble in water, and lacking an affinity for water. When hydrophobic compounds are mixed with hydrophilic substituents, such as vicinal diols, which have amphiphilic character, the mixture may form emulsions in water, with or without added surfactant.

As used herein, HLB (Hydrophile-Lipophile Balance) is an empirical expression for the relationship of the hydrophilic (water-loving) and hydrophobic (water-hating) surfactant properties, with HLB>10 having an affinity for water and numbers<10 having an affinity for oil (lipophilic).

As used herein, "hydrogel" refers to a water-swollen three-dimensional polymer network that is insoluble in aqueous medium.

As used herein, "thermosensitive polymer" refers to a polymer that responds to a change in temperature with a change in at least one of its physical, chemical or mechanical properties. Hydrogels made from thermosensitive materials exhibit a phase transition mediated by temperature that causes changes in their volume and rheological properties, such as viscosity and viscoelasticity.

As used herein, the term "room temperature" can be a range between 18° C. and 27° C., and more particularly between 20° C. and 25° C.

As used herein, the term "body temperature" is the average temperature of the human body usually comprising a range between 36.0° C. and 37.5° C.

As used herein, an "antimicrobial agent" kills or inhibits the growth of microorganisms. Antimicrobial agents can be grouped according to the microorganisms they act primarily against. For example, anti-bacterial agents act against bacteria, anti-fungal agents act against fungi, anti-viral agents act against viruses, and anti-protozoan agents act against protozoa.

As used herein, "anti-inflammatory agents" include, but are not limited to, water-soluble derivatives of aspirin, vitamin C, methylsulfonylmethane, tea tree oil, and non-steroidal anti-inflammatory drugs.

As used herein, an "antiseptic agent" inhibits the growth of microorganisms applied externally.

As used herein, "antiviral agents" treat infections caused by virus. Antiviral agents do not destroy the targeted pathogen but inhibit its development.

As used herein, "antifungal agents" destroy or prevent the growth of fungi.

As used herein, "active pharmaceutical ingredients (APIs)" refer to chemical compounds that are therapeutically or prophylactically effective and that induce a desired biological effect.

In some embodiments, the gel-forming compositions described herein can provide sustained delivery and/or release of antimicrobial agents to a wound surface.

In some embodiments, the gel-forming compositions described herein can provide a pH that is mildly acidic to enhance wound healing.

As used herein, low molecular weight water-soluble collagen is often referred to as collagen peptides, which are small bioactive peptides often from the enzymatic hydrolysis of collagen.

In some embodiments, the biologically active agent is biodegradable by human and animal cells.

In some embodiments, the biologically active agent is both biodegradable and non-cytotoxic to human and animal cells.

In some embodiments, the poloxamer gel compositions contain one or more biologically active agents. In some embodiments, any one of the biologically active agents can independently be present in an amount ranging from 0.001 wt-% to 25 wt-%, or from 0.01 wt-% to 20 wt-%, or from 0.1 wt-% to 10 wt-%, or from 1 wt-% to 5 wt-%, or any combination of these starting and ending points.

A non-limiting list of examples of biologically active agents includes, but it not limited to, antibiotics, antimicrobial agents, antifungal agents, antiviral agents, anti-bacterial agents, anti-protozoan agents, anti-pruritic agents, anti-acne agents, arthritis agents, rosacea agents, psoriasis agents, analgesics, anesthetics, astringents, anorectals, antihistamines, anti-inflammatory agents, non-steroidal anti-inflammatory drugs (NSAIDS), moisturizers, antimitotics, anti-cancer actives, scabicides, pediculicides, antiperspirants, deodorants, eczema agents, antipsoriatic agents, antiseborrheic agents, biologically active proteins and peptides, low molecular weight water-soluble collagen, collagen peptides, gelatin, thermal and radiation burn treatment agents, cancer treatment agents, wart removal agents, depigmenting agents, diaper rash treatment agents, keratolytic agents, enzymes, joint pain agents, hair growth stimulants, vitamins, hemostatics, canker sore treatment agents, cold sore treatment agents, dental and periodontal treatment agents, photosensitizing actives, skin protectant/barrier agents, skin treatment agents, steroids including hormones and corticosteroids, sunburn treatment agents, sunscreens, transdermal actives, nasal actives, vaginal actives, wart treatment agents, wound debriding agents, wound treatment agents, wound healing agents, wound antimicrobial agents, and retinoids (including retinol, retinoic acid and retinoic acid derivatives).

In some embodiments, low molecular weight water-soluble collagen, also known as collagen peptides, are added as a biodegradable gel or powder to aid in wound healing. In some embodiments, the percentage of low molecular weight water-soluble collagen is less than 60 wt-% of the poloxamer gel composition, or less than 50 wt-%, or less than 40 wt-%. In some embodiments, the percentage of low molecular weight water-soluble collagen is at least 2 wt-% of the poloxamer gel composition, or at least 5 wt-%, or at least 7 wt-%.

In some embodiments, topical antibiotic agents useful in the poloxamer gel compositions described herein include, but are not limited to, neomycin, kynamycin, streptomycin, erythromycin, clindamycin, rifampin, rifamycin, penicillin G, penicillin V, ampicillin, amoxicillin, bacitracin, polymixin, tetracycline, chlorotetracycline, oxytetracycline, doxycycline, cephalexin, cephalothin, chloramphenicol, gentamycin, neomycin, kanamycin, streptomycin, erythromycin, clindamycin, rifamycin, bactracin, polymyxin, chlorotetracycline, oxytetracycline, doxycycline; cephalexin, and cephalothin.

In some embodiments, topical antimicrobial agents for planktonic bacteria and biofilms useful in the poloxamer gel compositions described herein include, but are not limited to, bisbiguanides, such as alexidine and chlorhexidine and their respective salts, polymeric biguanides, such as poly (hexamethylene biguanide) and its salts, and other cationic polymers, such as polyquaternium-1, polyquaternium-6, polyquaternium-10, cationic guar, water-soluble derivatives of chitosan, polydiallyldimethylammonium salts, poly(N,N-dimethylaminoethyl methacrylate), poly(N,N-dimethylaminopropyl acrylamide), polyvinylamine and combinations thereof. Antimicrobial metals such as copper, zinc, tin and silver, and salts thereof, can also be incorporated into the formulation as dispersed or micellarized components.

In some embodiments, topical antifungal agents useful in the poloxamer gel compositions described herein include, but are not limited to, clotrimazole, miconazole, ketoconazole, itraconazole, fluconazole, metronidazole, astemizole, omeprazole, econazole, oxiconazole, sulconazole, ketoconazole, terbinafine, tolnaftate, undecylenic acid, naftifine, butenafine, and mixtures thereof.

In some embodiments, topical antiviral agents useful in the poloxamer gel compositions described herein include, but are not limited to, acyclovir, foscarnet sodium, ribavirin, vidarabine, ganeiclovir sodium, zidovudine, phenol, amantadine hydrochloride, interferon alfa-n3 and podophyllotoxin.

In some embodiments, topical thermal burn treatment agents useful in the poloxamer gel compositions described herein include, but are not limited to, silver sulphadiazine, cerium nitrate-silver sulphadiazine, mafenide acetate, silver nitrate solution 0.5%, debriding agents, chlorhexidine, povidone iodine, mupirocin, hydrocolloid dressings, hydrogel dressings, gentamicin, bacitracin, norfloxacin, and bismuth tribromophenate petroleum blend.

Wounds are an ideal environment for the formation of biofilm communities because of their susceptibility to contamination and the availability of substrate and nutrients for biofilm attachment. Chronic wound infections share two important attributes with other biofilm diseases: persistent infection that is not cleared by the host immune system, and resistance to systemic and topical antimicrobial agents.

Common bacteria found in biofilms include Gram positive *Enterococcus faecalis, Staphylococcus aureus, Micrococcus* spp. and beta-hemolytic *Streptococcus* (*S. pyogenes, S. agalactiae*) as well as Gram-negative bacteria of *Escherichia coli, Klebsiella pneumoniae, Proteus mirabilis, Pseudomonas aeruginosa, Acinetobacter baumannii* and *Stenotrophomonas maltophilia., Proteus* spp., *Citrobacter* spp. and *Enterobacter* spp. In addition, both facultative and strictly anaerobic bacterial genera have been detected in wound biofilm, including *Anaerococcus* spp., *Finegoldia* spp., *Parvimonas* spp., *Peptoniphilus* spp. *Peptostreptococcus* spp. *Staphylococcus* spp., *Bacteroides* spp., *Anaerococus* spp., *Peptoniphilus* spp., *Porphyromonas* spp., *Fusobacterium* spp *Prevotella* spp. and *Finegoldia* spp.

Fungi are also found in wounds. Such fungi include *Candida* spp. and *Cladosporidium* spp. in addition to *Aspergillus* spp., *Penicillium* spp., *Alternaria* spp., *Pleospora* spp., *Fusarium* spp., *Trichosporon asahii, Rhodotorula* spp., and *Trichtophyton* spp., among others.

The wound environment may promote multispecies biofilm formation between bacteria and fungi in wounds.

Embodiments of the disclosure described herein are also applicable for treating a microbial biofilm on a patient or inanimate surface by contacting the microbial biofilm with a composition comprising a gelled poloxamer composition in aqueous media containing antimicrobial agents and/or active pharmaceutical ingredients (API).

In some embodiments, topical antiprotozoal drugs useful in the poloxamer gel compositions described herein include, but are not limited to, chloroquine, pyrimethamine, mefloquine, hydroxychloroquine; metronidazole, eflornithine, furazolidone, melarsoprol, nifursemizone, nitazoxanide, ornidazole, paromomycin sulfate, pentamidine, quinapyramine, and tinidazole.

In some embodiments, topical anti-inflammatory agents useful in the poloxamer gel compositions described herein include, but are not limited to, water-soluble derivatives of aspirin, vitamin C, methylsulfonylmethane, acetylsalicyclic acid, celecoxib, diclofenac, diflunisal, etodolac, ibuprofen, indomethacin, ketoprofen, ketorolac, nabumetone, naproxen, oxaprozin, piroxicam, salsalate, sulindac, tolmetin, indomethacin, meclofenamate sodium, fenoproben calcium, mefenamic acid, nabumetone, ketorolac tromethamine, evening primrose oil, jojoba oil, mesalamine, salicylsalicylic acid, choline magnesium trisalicylate, flunisolide, triamcinolone, triamcinolone acetonide, beclomethasone diproprionate, betamethasone diproprionate, hydrocortisone, cortisone, dexamethasone, prednisone, methyl prednisolone, zinc and prednisolone.

In some embodiments, topical radiation burn treatment agents useful in the poloxamer gel compositions described herein include, but are not limited to, corticosteroids, topical antibiotics, aloe vera, and calendula ointment.

In some embodiments, topical analgesics for the relief of pain useful in the poloxamer gel compositions described herein include, but are not limited to, acetaminophen, aspirin, ibuprofen, naproxen, diclofenac, opioids, COX-2 inhibitors, cannabidiol, and NSAIDS.

In some embodiments, topical arthritis and joint pain agents useful in the poloxamer gel compositions described herein include, but are not limited to, cannabidiol, nonsteroidal anti-inflammatory drugs, corticosteroids, TNF-inhibitors, disease modifying anti-rheumatic drugs, acetaminophen, codeine, capsaicin, methyl salicylate, methotrexate, sulfasalazine and analgesic agents.

In some embodiments, joint pain agents useful in the poloxamer gel compositions described herein include, but are not limited to, acetaminophen, codeine, corticosteroids, capsaicin, methyl salicylate, NSAIDS, methotrexate and sulfasalazine.

In some embodiments, topical treatments for cold sores, also called fever blisters, usually caused by herpes simplex virus 1 (HSV-1), useful in the poloxamer gel compositions described herein include, but are not limited to, acyclovir, valacyclovir, famciclovir, penciclovir, docosanol, aloe vera, aspirin, ibuprofen, acetaminophen, lidocaine, benzocaine, dibucaine, menthol, camphor, benzyl alcohol, allantoin, petrolatum, cocoa butter, glycerin, zinc compositions, antimicrobial agents, tee tree oil, hydrocortisone, benzocaine, camphorated phenol, dimethicone, lidocaine and allantoin.

In some embodiments, topical canker sore (mouth ulcer) treatments useful in the poloxamer gel compositions described herein include, but are not limited to, benzocaine, lidocaine, hydrogen peroxide, carbamide peroxide, fluocinonide, chlorhexidine, doxycycline, tetracycline, minocycline, hydrocortisone hemi succinate, eucalyptus, menthol, beclomethasone, dexamethasone, corticosteroids, benzydamine, diclofenac and antifungal agents.

In some embodiments, periodontal treatments useful in the poloxamer gel compositions described herein include, but are not limited to, chlorhexidine, doxycycline, minocycline, amoxicillin, metronidazole, tetracycline, and hydrogen peroxide.

In some embodiments, topical eczema agents for treating inflammation of the skin characterized by itchiness, red skin, blisters and rash, useful in the poloxamer gel compositions described herein include, but are not limited to, corticosteroid creams, tacrolimus, pimecrolimus, crisaborole and moisturizers.

In some embodiments, topical scabicides for killing scabies mites useful in the poloxamer gel compositions described herein include, but are not limited to, permethrin, crotamiton, sulfur ointment, lindane, benzyl benzoate, and keratolytic cream.

In some embodiments, topical pediculicides for the treatment of head lice useful in the poloxamer gel compositions described herein include, but are not limited to, lindane, malathion, carbaryl, pyrethrum, permethrin, phenothrin, and allethrin, proteases, and dimethicone.

In some embodiments, topical anti-seborrheics effective in seborrheic dermatitis (dandruff) useful in the poloxamer gel compositions described herein include, but are not limited to, selenium sulfide, zinc pyrithione, corticosteroids, imidazole antifungals, salicylic acid, sodium sulfacetamide, tea tree oil, eucalyptus oil, ketoconazole, sulfur and coal tar.

In some embodiments, topical wart removal agents useful in the poloxamer gel compositions described herein include, but are not limited to, salicylic acid, cantharidin, tretinoin, and glycolic acid.

In some embodiments, topical depigmenting agents that inhibit melanogenesis (the pigmentation pathway by which cells produce melanin) useful in the poloxamer gel compositions described herein include, but are not limited to, hydroquinone, 4-hydroxyanisole, fluocinolone, tretinoin, adapalene, monobenzyl ether of hydroquinone, azelaic acid, kojic acid, niacinamide, and serine protease inhibitors.

In some embodiments, topical anti-pruritic agents useful in the poloxamer gel compositions described herein include, but are not limited to, antihistamines (diphenhydramine, hydroxyzine), enzymes, corticosteroids, doxepin, anesthetics, such as lidocaine, prilocaine, pramoxine, capsaicin, polidocanol, menthol, N-palmitoylethanoamine, topical calcineurin inhibitors, and topical vitamin D modulators.

In some embodiments, topical treatments for diaper rash (or irritant diaper dermatitis) useful in the poloxamer gel compositions described herein include, but are not limited to, barrier creams, petroleum jelly, mild topical cortisones, zinc creams, topical antibiotics, calendula extract and antifungal agents.

In some embodiments, enzymes in topical skin treatment useful in the poloxamer gel compositions described herein include, but are not limited to, bromelain, papain, ficin, amylase, actinidin, collagenase, phospholipase, and lipase.

In some embodiments, topical rosacea agents useful in the poloxamer gel compositions described herein include, but are not limited to, brimonidine, azelaic acid, metronidazole, and sulfacetamide.

In some embodiments, topical psoriasis agents, particularly for plaque psoriasis, useful in the poloxamer gel compositions described herein include, but are not limited to, topical corticosteroids, topical retinoids, anthralin, vitamin D3, salicylic acid, and moisturizers.

In some embodiments, topical anorectals, particularly or hemorrhoids, useful in the poloxamer gel compositions described herein include, but are not limited to, hydrocortisone, witch hazel, aloe vera, and lidocaine.

In some embodiments, topical keratolytic agents for softening and facilitating exfoliation of epidermal cells useful in the poloxamer gel compositions described herein include, but are not limited to, salicylic acid, urea, lactic acid, allantoin, glycolic acid, resorcinol, benzoyl peroxide, and trichloroacetic acid.

In some embodiments, topical astringents that are drying agents that precipitate protein and shrink and contract the skin useful in the poloxamer gel compositions described herein include, but are not limited to, aluminum triacetate, aluminum sulfate plus calcium acetate, alum, calamine, acacia, sage, yarrow, witch hazel, bayberry, distilled vinegar, very cold water, rubbing alcohol, glycerin, silver nitrate, potassium permanganate, zinc oxide, zinc sulfate, tincture of benzoin, and tannic and gallic acids.

In some embodiments, topical moisturizers used for protecting, moisturizing, and lubricating the skin useful in the poloxamer gel compositions described herein include, but are not limited to: (i) emollients, including cholesterol, fatty acids, fatty alcohols, squalene, and pseudoceramides, (ii) humectants, including glycerol, propylene glycol, panthenol, sorbitol, urea, alpha-hydroxy acids, and hyaluronic acid, (iii) occulsives, including petrolatum, beeswax, mineral oil, silicones, cyclomethicone, lanolin, and zinc oxide, and (iv) protein rejuvenators, including collagen, gelatin, elastin, and keratin.

In some embodiments, topical corticosteroids, a class of steroid hormones, useful in the poloxamer gel compositions described herein include, but are not limited to, cortisol, corticosterone, aldosterone, hydrocortisone, methylprednisolone, prednisolone, prednisone, triamcinolone, amcinonide, budesonide, desonide, fluocinolone, acetonide, fluocinonide, halcinonide, triamcinolone acetonide, beclometasone, betamethasone, dexamethasone, fluocortolone, halometasone, and mometasone, alclometasone dipropionate, betamethasone dipropionate, betamethasone valerate, clobetasol propionate, clobetasone butyrate, fluprednidene acetate, mometasone furoate, fluticasone, ciclesonide, cortisone acetate, hydrocortisone aceponate, hydrocortisone acetate, hydrocortisone buteprate, hydrocortisone butyrate, hydrocortisone valerate, prednicarbate, and tixocortol pivalate.

In some embodiments, topical anti-acne agents useful in the poloxamer gel compositions described herein include, but are not limited to, benzoyl peroxide, glycolic acid, lactic acid, salicylic acid, sulfur, tee tree oil, tretinoin, erythromycin, clindamycin, tetracycline, doxycycline, minocycline, azelaic acid, isotretinoin, tretinoin, adapalene, tazarotene, and Manuka essential oil.

In some embodiments, topical treatment chemotherapy drugs as anticancer medications applied directly to the skin useful in the poloxamer gel compositions described herein include, but are not limited to, 5-fluorouracil, diclofenac, ingenol mebutate, and imiquimod.

In some embodiments, topical antiperspirants, which attempt to stop or significantly reduce perspiration, useful in the poloxamer gel compositions described herein include, but are not limited to, aluminum chlorohydrate, aluminum zirconium tetrachlorohydrex gly, and aluminum zirconium trichlorohydrex gly.

In some embodiments, topical deodorants, which are designed to eliminate odor, useful in the poloxamer gel compositions described herein include, but are not limited to, perfumes, essential oils, sodium stearate, stearyl alcohol, potassium alum, and ammonium alum.

In some embodiments, hair growth stimulants useful in the poloxamer gel compositions described herein include, but are not limited to, minoxidil, finasteride, biotin, and dihydrotestosterone.

In some embodiments, vitamins for skin treatment useful in the poloxamer gel compositions described herein include, but are not limited to, vitamin A, vitamin C, vitamin E, vitamin D, vitamin K, vitamin B1, vitamin B3, vitamin B5, vitamin B6, biotin, choline, folic acid, and vitamin E analogs (6-hydroxy-2,5,7,8-tetramethylchroman-2-carboxylic acid).

In some embodiments, topical antioxidants useful in the poloxamer gel compositions described herein include, but are not limited to, selenium, vitamin A, vitamin C, vitamin E, vitamin K, coenzyme Q10, curcumin, resveratrol, retinol, epigallocatechin-3 gallate, polyphenol, flavonoids, glutathione, beta-carotene, lutein, lycopene, zeaxanthin, resveratrol, zinc, manganese, cysteine, curcumin, astaxanthin, alpha lipoic acid, carnosine, glutathione, polyphenols, quercetin, soy isoflavones, superoxide dismutase, *Allium* species, catalase, ellagic acid, and melatonin.

In some embodiments, the sunscreen agents can be chemical or physical sunscreen agents. Physical sunscreen agents useful in the poloxamer gel compositions described herein include, but are not limited to, zinc oxide and titanium dioxide that provide broad spectrum UVA (320-400 nanometers) and UVB (290 to 320 nanometers) protection and are gentle to skin. Chemical sun-blocking agents, however, may be solubilized or suspended and added to a sunscreen formulation that results in a transparent or translucent coating on skin. In some embodiments, the chemical sunscreen components include, but are not limited to, avobenzone (butylmethoxydibenzoylmethane; 4-tert-butyl-4'-methoxydibenzoylmethane), homosalate (homomenthyl salicylate; 3,3,5-trimethylcyclohexyl 2-hydroxybenzoate), octisalate (octyl salicylate; 2-ethylhexyl salicylate; 2-ethylhexyl 2-hydroxybenzoate), octocrylene (2-ethylhexyl-2-cyano-3,3-diphenyl-2-acrylate; 2-ethylhexyl-2-cyano-3,3-diphenyl-2-propenoate), oxybenzone (benzophenone-3; (2-hydroxy-4-methoxyphenyl)phenylmethanone; 2-hydroxy-4-methoxybenzophenone), otinoxate (ethylhexyl methoxycinnamate; octyl methoxycinnamate), and combinations thereof. Avobenzone absorbs in the UVA, homosalate absorbs in the UVB, octisalate absorbs in the UVB, octocrylene absorbs in the UVB, oxybenzone absorbs in the UVA and UVB, and otinoxate absorbs in the UVB. In order to slow the photodegradation of avobenzone and otinoxate, photostabilizers can be added, such as Polysilicone-15 (polydimethylsiloxane-based oligomeric UV absorber), undecylcrylene dimethicone, diethylhexyl-2,6-naphthalate, ethylhexyl methoxycrylene, and the like.

In some embodiments, topical sunburn agents useful in the poloxamer gel compositions described herein include, but are not limited to, emollient creams, topical aloe vera, and over-the-counter analgesics.

In some embodiments, topical wound healing agents useful in the poloxamer gel compositions described herein include, but are not limited to, hyaluronic acid, antimicrobial dressings, growth factors, stem cells, collagen, oxygen, nutrients including proteins, carbohydrates, arginine, glutamine, polyunsaturated fatty acids, vitamin A, vitamin C, vitamin E, magnesium, copper, zinc and iron, biodegradable scaffolds, heparan sulfates, gold nanoparticles, biofilm disruption and elimination, nitric oxide, polymeric biomaterials, polyhexamethylene biguanide, chlorhexidine salts, silver and silver salts.

In some embodiments, topical retinoids for the regulation of epithelial cell growth useful in the poloxamer gel compositions described herein include, but are not limited to, retinol, retinoic acid, alitretinoin, Isotretinoin, acitretin, adapalene, bexarotene, tazarotene, and retinoic acid derivatives.

In some embodiments, vaginal active agents useful in the poloxamer gel compositions described herein include, but are not limited to, clotrimazole, miconazole nitrate, nonoxynol-9, dequalinium chloride, imiquimod, and hydrocortisone.

EXAMPLES

Various embodiments will be further clarified by the following examples.

All formulations were prepared as received using the poloxamer and viscosity enhancing agents, inclusive of monoalkyl glycols, monoalkyl glycerols, and monoacyl glycerols from the manufacturers listed in Table 1. Since the surfactant is thermoresponsive and does increase in viscosity to form a non-flowable gel at a specific concentration and temperature, its sol-gel temperature was used as a positive control in comparing the C6, C8, C12, and C16 vicinal diols of this disclosure at concentrations of 0.1 wt. %, 0.3 wt. %, 0.6 wt. %, 0.9 wt. %, 1.2 wt. %, 1.5 wt. %, and 1.8 wt. %. The concentration of Poloxamer 407 was chosen as 17 wt. %, with an average sol-gel temperature of 29.7° C. The concentration of Poloxamer 188 was chosen at 46 wt. %, with an average sol-gel temperature of 29° C.

TABLE 1

List of Vicinal Diol Ingredients and Poloxamers

| $C_x$ | Name | Company | Lot # |
|---|---|---|---|
| $C_{6diol}$ | Hexanediol | Center of Innovative Drug Discovery | SM2018-86-76 |
| $C_{6ether}$ | Hexyl glycerol | Sigma Aldrich | STBG2429V |
| $C_{8diol}$ | Octanediol | Sigma Aldrich | STBH1186 |
| $C_{8ether}$ | Octyl glycerol | Center of Innovative Drug Discovery | SM2018-86-74 |
| $C_{8ether}$ | Ethylhexyl glycerol | Schulke & Mayr | 1272204 |
| $C_{8ester}$ | 1-Octanoyl-rac-glycerol | Sigma Aldrich | SLBW6117 |
| $C_{12diol}$ | Dodecanediol | Sigma Aldrich | STB1186 |
| $C_{12ether}$ | 1-O-Dodecyl-rac-glycerol | Santa Cruz Biotechnology | H1911 |
| $C_{12ester}$ | Lauricidin | Med-Chem Labs | 4010608422 |
| $C_{16diol}$ | Hexadecanediol | TCI | I43VI-EN |
| $C_{16ether}$ | 1-O-Hexadecyl-rac-glycerol | ChemCruz | C1419 |
| $C_{16ester}$ | Monopalmitin | TCI | HEX01-QTME |
| $C_0$ | Poloxamer 407 | Spectrum | 2HA0214 & 1HH0918 |
| $C_0$ | Poloxamer 188 | BASF | WPYJ544B |

TABLE 2

List of Added Suspended or Dissolved Ingredients:

| | Name | Company | Lot # |
|---|---|---|---|
| 1 | EDTA | Spectrum | IDK0688 |
| 2 | Guar | Sigma | SLBH5231V |
| 3 | PEG | Sigma | MKBH6594V |
| 4 | Avobenzene | Merck | 5844G124313 |
| 5 | Lidocaine | Topicaine | 19671 |
| 6 | PHMB | Lonza | 14GR100230 |
| 7 | Zinc Oxide | Spectrum | 1GG0274 |
| 8 | Miconazole Nitrate | Sigma | BCBD5966V |
| 9 | Terbinafine | Sigma | SLBR5903V |
| 10 | Acetylsalicylic Acid | Spectrum | 2GC0115 |
| 11 | Medihoney | DermaSciences | WPYJ544B |

TABLE 2-continued

List of Added Suspended or Dissolved Ingredients:

| | Name | Company | Lot # |
|---|---|---|---|
| 12 | Silver Sulfadiazine | Sigma Aldrich | MKBP8119V |
| 13 | Amylase | Deerland | 133806 |

Each of the vicinal diols studied has multiple chemical names. Thus, for ease of representing the various hydrophobic vicinal diols, which are represented by the symbols $C_6$, $C_8$, $C_{12}$, and $C_{16}$, with $C_{8diol}$, $C_{8ether}$, and $C_{8ester}$ representing 8-carbon monoalkyl glycols, monoalkyl glycerols, and monoacyl glycerols, respectively, and $C_{12diol}$, $C_{12ether}$, and $C_{12ester}$ representing 12-carbon monoalkyl glycols, monoalkyl glycerols, and monoacyl glycerols, respectively. The same terminology is used for the $C_6$ and $C_{16}$ vicinal diols. The poloxamers studied are Poloxamer 407, also named Pluronic® F-127, and Poloxamer 188, also named Kolliphor® P 188 and Pluronic® F-68.

Measurement of the Sol-Gel Transitions:

The sol-gel transition temperatures were determined by a test tube inverting method with a temperature increment of 1° C. per step. Aqueous poloxamer solutions (0.5 g) were prepared in 4 mL vials with inner diameters of 11 mm. The vials were immersed in a water bath at each step for 15 minutes. The sol-gel transition temperature was monitored by inverting the vials, and if there was no flow in 30 seconds, it was regarded as a gel. The transition temperature was determined with ±1° C. accuracy.

Samples and sol-gel temperatures were prepared and analyzed. The data shows that the addition of monoalkyl glycols, monoalkyl glycerols, and monoacyl glycerols can affect the sol-gel temperatures of both the specific poloxamers and other poloxamers. Table 3 shows that octyl glycerol, in this case, decreases the overall sol-gel temperature of 46% Poloxamer 188 by approximately 5° C. with the concentrations utilized, while lowering the sol-gel temperature of 17% Poloxamer 407 by up to 10° C. This shows that $C_{8ether}$ monoalkyl glycerols are able to decrease the sol-gel temperatures of both more hydrophobic poloxamers (such as poloxamer 407, HLB 22) and more hydrophilic poloxamers (such as poloxamer 188, HLB 29) based upon HLB values.

Sample Preparation

Samples were prepared using the material list of Table 1.

Six and eight carbon chains ($C_6$ and $C_8$): 10 mL of each sample of the $C_{6diol}$, $C_{6ether}$, $C_{8diol}$, $C_{8ether}$, or $C_{8ester}$ at the above weight percentages was prepared using water as a diluent. The calculated amount of water was weighed and placed in a beaker. The beaker was placed in an ice bath (approximately 13° C.-15° C.) and the desired wt. % of surfactant Poloxamer 407 or Poloxamer 188 was added and stirred until complete dissolution. The $C_6$ or $C_8$ monoalkyl glycol, monoalkyl glycerol, or monoacyl glycerol was placed into the beaker, and stirred slowly. The beaker was removed from the ice-bath and placed on a stir plate with continued stirring at RTP until the vicinal diols were completely dissolved. The composition was then placed in a disposable test tube where it could form a gel at room temperature.

Twelve and sixteen carbon chains ($C_{12}$ and $C_{16}$): 10 mL of each sample of the $C_{12diol}$, $C_{12ether}$, $C_{12ester}$, $C_{16diol}$, $C_{16ether}$, or $C_{16ester}$ at the above weight percentages was prepared using water as a diluent. The calculated amount of water was weighed and placed in a beaker, then the desired wt. % of $C_{12}$ or $C_{16}$ monoalkyl glycol, glycerol monoalkyl ether, or monoacyl glycerol along with ⅓ of the 17% surfactant weighed was placed into the beaker, and stirred at 50° C.-70° C., to allow for complete solvation. The temperature was turned off, the beaker was placed in an ice bath and the remaining ⅔ of 17 wt. % of the surfactant was added and stirred until complete dissolution. The composition was then placed in a disposable test tube where it could form a gel at room temperature.

FIG. 1 shows the sol-gel temperature results for the compositions made as specified, using $C_6$ vicinal diols, which also shows the indirect relationship between the sol-gel temperature of Poloxamer 407 with increasing amounts of 6-carbon monoalkyl glycol or monoalkyl glycerol.

An overall temperature drop of 1.5° C. and 2.7° C. was observed from the addition of hexanediol and hexyl glycerol, respectively. Thus, illustrating the capability of the 6-carbon vicinal diols to decrease the sol-gel temperature of Poloxamer 407.

Figure 2:
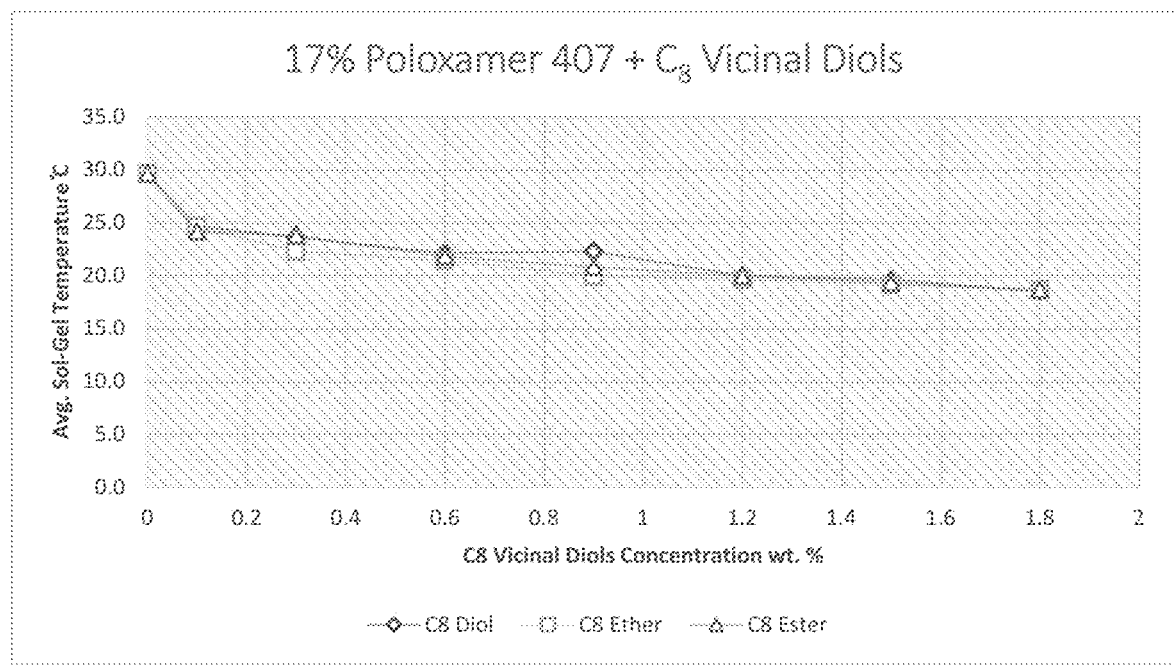
FIG. 2 is a graph showing the average sol-gel temperatures of Poloxamer 407 after the addition of $C_8$ monoalkyl glycols, monoalkyl glycerols, and monoacyl glycerols at 0-1.8 wt. %.

FIG. 2 shows the sol-gel temperature results using Poloxamer 407 with increasing amounts of $C_8$ monoalkyl glycol, monoalkyl glycerol, and monoacyl glycerol. The positive control of 17 wt. % Poloxamer 407 sample is represented by the highest point on the graph, which shows an average sol-gel temperature of 29.7° C. (from three readings). After the addition of 0.1% of octanediol, octylglycerol, and octanoylglycerol, an initial sharp decrease of the sol-gel temperature by approximately 5-6° C. was observed for each $C_8$ vicinal diol tested. In general, the sol-gel temperature continued to gradually decrease as the wt. % of $C_8$ monoalkyl glycol, monoalkyl glycerol, or monoacyl glycerol increased, after the initial 5-6° C. drop.

Figure 3:
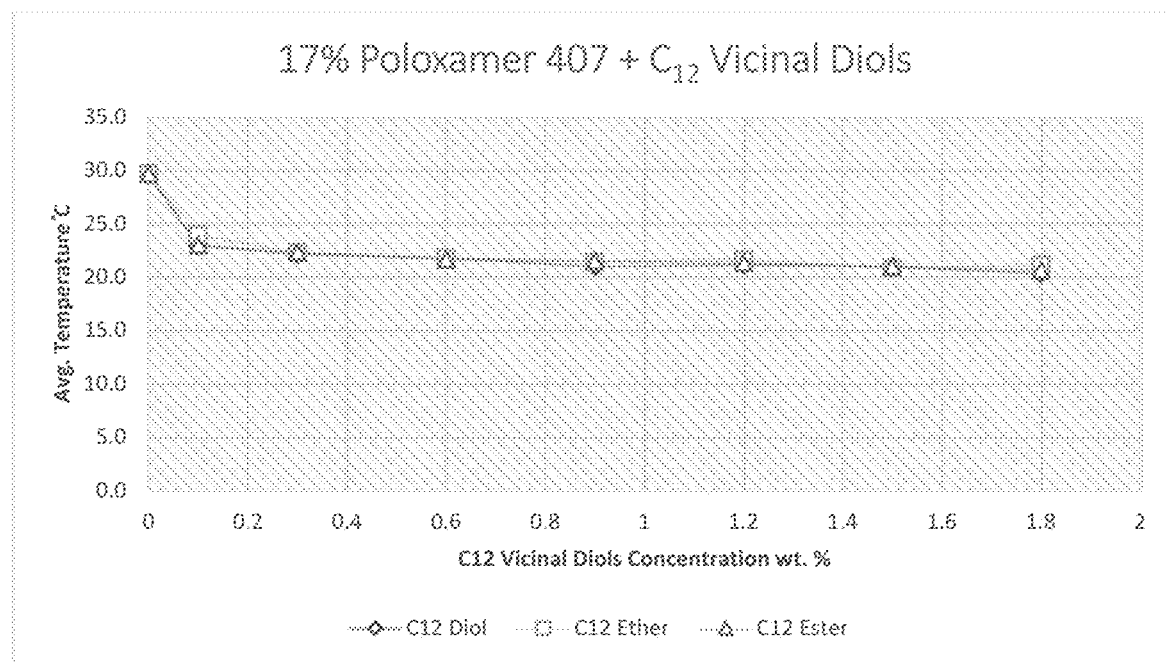
FIG. 3 is a graph showing the average sol-gel temperatures of Poloxamer 407 after the addition of $C_{12}$ monoalkyl glycols, monoalkyl glycerols, and monoacyl glycerols at 0-1.8 wt. %.

FIG. 3 shows the sol-gel temperature results using Poloxamer 407 with increasing amounts of $C_{12}$ monoalkyl glycol, monoalkyl glycerol, and monoacyl glycerol added. As in FIGS. 1 and 2, the positive control of Poloxamer 407 alone (without added vicinal diol) is represented by the highest point on the graph, which shows an average sol-gel temperature of 29.7° C. As with the $C_8$ vicinal diols, after the addition of 0.1% of dodecanediol, dodecyl-1-glycerol, and

TABLE 3

Changes in the sol-gel temperatures of both Poloxamer 407 and Poloxamer 188 in the presence of Octyl Glycerol ($C_{8ether}$) at concentrations 0-1.2 w %.

| | | Octyl glycerol (wt. %) | | | | | |
|---|---|---|---|---|---|---|---|
| | | 0 | 0.1 | 0.3 | 0.6 | 0.9 | 1.2 |
| 46% Poloxamer 188 | Avg. Sol-gel Temp (° C.) | 29.0 | 25.0 | 22.2 | 24.0 | 24.2 | 24.0 |
| | Stdev | 1.0 | 0.0 | 0.3 | 0.0 | 0.6 | 0.0 |
| 17% Poloxamer 407 | Avg. Sol-gel Temp (° C.) | 29.7 | 24.7 | 22.3 | 21.5 | 20.0 | 19.7 |
| | Stdev | 0.3 | 0.3 | 0.3 | 0.0 | 0.0 | 0.3 | dodecanoyl-1-glycerol a sharp decrease of sol-gel temperature by approximately 5-7° C. was found for each $C_{12}$ vicinal diol tested. In general, the sol-gel temperature continued to gradually decrease as the wt. % of $C_{12}$ monoalkyl glycol, monoalkyl glycerol, or monoacyl glycerol increased, after the initial 5-7° C. drop.

It is thus seen that the average sol-gel temperature of Poloxamer 407 can be decreased by up to 7° C. with as little as 0.1 wt. % vicinal diol, with an apparent maximum decrease of 10-12° C.

Figure 4:
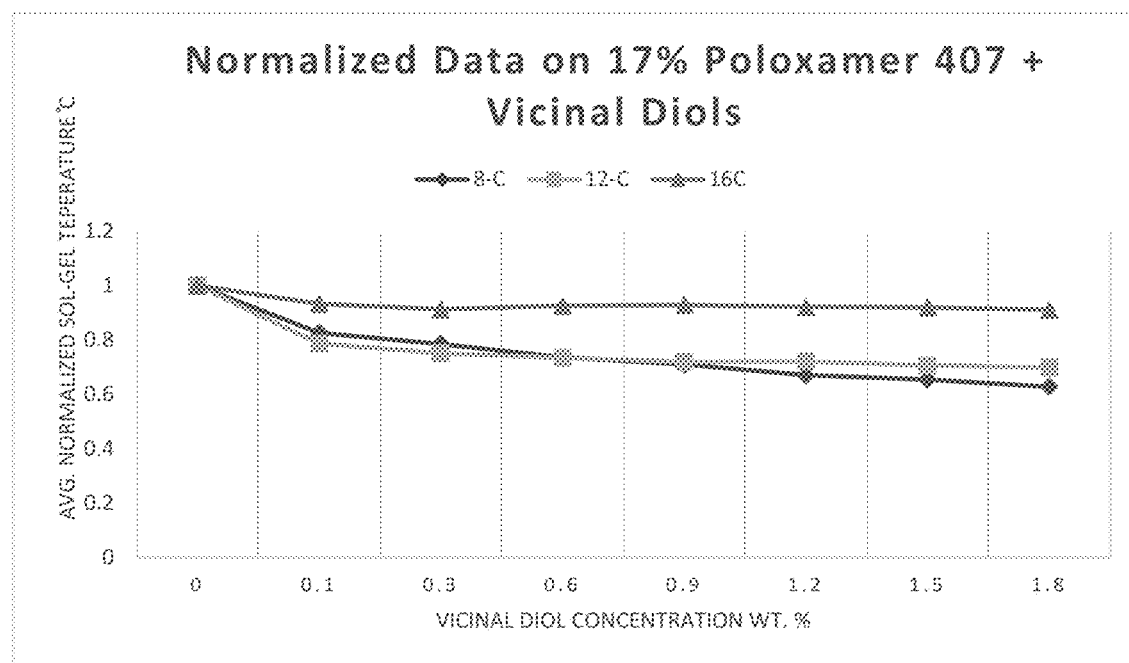
FIG. 4 is a graph showing the normalized data of sol-gel temperature changes for vicinal diols ($C_8$ to $C_{16}$), utilizing the $C_0$ sol-gel temperatures.

FIG. 4 shows normalized data for vicinal diols with 8-carbons to 16-carbons. The data has been normalized using the sol-gel temperatures of Poloxamer 407 in each formulation. Thus, the initial reading of one (1) corresponds to the positive control (poloxamer without vicinal diol added ($C_0$). The sol-gel temperature of Poloxamer 407 initially decreased approximately 5° C. with the addition of 0.1 wt. % $C_8$ and $C_{12}$ vicinal diols. Moreover, there is an approximate 10° C. overall decrease of Poloxamer 407's sol-gel temperature when $C_8$ and $C_{12}$ are present at 1.8 wt. %. The $C_{16}$ vicinal diols sol-gel temperature initial decrease was approximately 2° C. while the overall decrease at 1.8 wt. % is approximately 3° C. which is similar to the effect with the $C_6$ vicinal diols, indicating that the 8- and 12-carbons are more effective at lowering the sol-gel temperatures that the 6-carbons or the 16-carbons. Nonetheless, the addition of $C_6$ or $C_{16}$ still conveys a lowering of sol-gel temperature; thus, vicinal diols ($C_6$ to $C_{16}$) are all effective at lowering the sol-gel temperatures of poloxamers, such as Poloxamer 407, with $C_8$ and $C_{12}$ being the most effective.

Sol-Gel Determination Using Drip Flow Method

The determination of whether a sol-gel was formed was made by pipetting 0.24 g poloxamer gel composition onto a glass surface which was tilted at an approximate 90° angle. With a black marking pen the glass surface was ruled into 0.5 cm lines in order to determine the distance over which the poloxamer gel composition would flow down the glass surface at room temperature (23.5° C.). The pipetted poloxamer gel composition was deposited as a circular drop at the highest elevation (just above the line for 0 cm). Readings were taken at 0, 1, 2, 3, 4, 5, 6, 7, 8, 9, 10, 20, 30 and 60 minutes. Readings of 0 cm at 60 minutes indicated no flow of the poloxamer gel composition and hence, the composition was above its sol-gel temperature and was regarded as a gel. Readings of 6 cm at 0 minutes (immediate flow) indicate the composition was flowing readily and hence, was below its sol-gel temperature and was regarded as a liquid.

Figure 5:
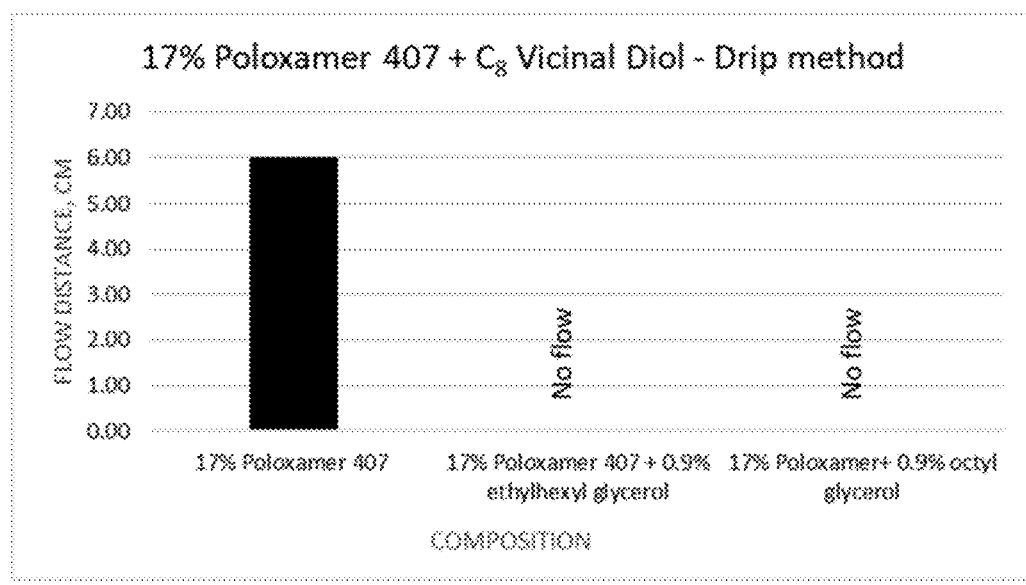
FIG. 5 is a graph showing the measured flow in centimeters of 17 wt % Poloxamer 407 as compared to Poloxamer 407 after the addition of $C_8$ linear and non-linear monoalkyl glycerols at 0.9 wt %.

Samples and sol-gel temperatures were prepared and analyzed using either a linear (octyl glycerol) or a branched glycerol (ethylhexyl glycerol). The data shows that the addition of either a linear or branched vicinal diol can affect the sol-gel temperature of poloxamer gel compositions. FIG. 5 shows that the addition of either octyl glycerol or ethylhexyl glycerol to 17% Poloxamer 407 provides a non-flowing gel while 17% Poloxamer 407 by itself flows the full extent of the 6 cm ruled glass surface. The results are the same at all time points between immediate (zero minutes) and 60 minutes. In other words, the 17% Poloxamer 407 flows immediately the full length of the glass surface (6 cm) and the poloxamer gel compositions containing the vicinal diols are gels that do not flow at any time points being evaluated.

Sample Preparation

Samples were prepared using the material list of Table 1.

Each sample was prepared using water as a diluent. The calculated amount of water was weighed and placed in a beaker. The beaker was placed in an ice bath (approximately 13° C.-15° C.) and 17 wt. % of surfactant Poloxamer 407 was added and stirred until complete dissolution. The 0.9 wt % $C_8$ monoalkyl glycerols, either octyl glycerol or ethylhexyl glycerol, was placed into the beaker, and stirred slowly. The beaker was removed from the ice-bath and placed on a stir plate with continued stirring at RTP (room temperature and pressure) until the vicinal diols were completely dissolved.

FIG. 5 shows sol-gel determination results using the drip flow method. At room temperature 17% Poloxamer 407 by itself is a solution whereas the addition of either a linear or a non-linear vicinal diol to the poloxamer provided a gel. Hence, this further measurement method (drip flow) also indicates the effect of vicinal diols, including branched vicinal diols, in decreasing the sol-gel temperature of poloxamers.

Importantly, the lowering of the sol-gel temperature causes a gel behavior further below body temperature with the same amount of poloxamer. This provides for the creation of compositions with greater residence time on a biological surface, such that a biologically active agent in the gelled poloxamer can be effectively delivered to the biological surface in need of treatment for an extended period-of-time.

Table 2 lists several active agents that can be suspended or dissolved in a solution of $C_{12}$ diol ($C_{12ester}$) in 17 wt. % Poloxamer 407. These active agents include:

Pharmaceutical Agent: Acetylsalicylic Acid
Wound Healing Agent: Manuka Honey
Enzymatic Agent: Amylase
Antimicrobial Agent: PHMB, Miconazole Nitrate, Terbinafine
Anti-itch Agent: Lidocaine
Anti-burn agent: Silver Sulfadiazine
Chelating Agent: EDTA (Ethylenediaminetetraacetic Acid)
Hydrophilic Polymer: Guar
UV Absorbing Agent: Avobenzene, Zinc Oxide Observations were made when various weight percentages of active agents were added to 17% Poloxamer 407+0.9% Dodecanediol gel. The results after 24 hours are reported in Table 4, below.

TABLE 4

Active Agents and Observations

| Number | Name | Observation |
|---|---|---|
| 1 | 0.5% EDTA | gel |
| 2 | 0.5% Guar | gel |
| 3 | 3% Avobenzene | gel |
| 4 | 5% Lidocaine | gel |
| 5 | 0.1% PHMB | gel |
| 6 | 1% PHMB | gel |
| 7 | 20% Zinc Oxide | suspension, gel |
| 8 | 2% Miconazole Nitrate | suspension, gel |
| 9 | 0.5% Terbinafine | gel |
| 10 | 1% Acetylsalicylic Acid | gel |
| 11 | 10% Medihoney | gel |
| 12 | 1% Silver Sulfadiazine | suspension, gel |
| 13 | 10% Amylase | suspension, gel |

Each of these formulations demonstrated stability for at least 24 hours as noted in Table 4. Of note, even the suspensions were stable for at least 24 hours.

While the above specification contains many specifics, these should not be construed as limitations on the scope of the disclosure, but rather as examples of preferred embodiments thereof. Many other variations are possible. Accordingly, the scope of the disclosure should be determined not by the embodiments illustrated, but by the appended claims and their legal equivalents.

The invention claimed is:

1. A poloxamer gel composition comprising:
0.05 to 5 wt. % hydrophobic vicinal diol component,
17 to 46 wt. % of a poloxamer component;
0.5 wt. % or less of a water soluble polymer other than poloxamer;
wherein the hydrophobic vicinal diol component is 6-carbon to 16-carbon length monoalkyl glycols, 6-carbon to 16-carbon length monoalkyl glycerols or a combination thereof;
wherein the monoalkyl group of the 6-carbon to 16-carbon length monoalkyl glycerols is 6-carbons to 16-carbons in length,
wherein the poloxamer component is selected from the group consisting of Poloxamer 407, Poloxamer 188, and a combination thereof, and
wherein the hydrophobic vicinal diol component depresses a sol-gel temperature of an aqueous poloxamer equivalent by at least 1° C.

2. The poloxamer gel composition of claim 1, wherein the hydrophobic vicinal diol component comprises a hydrophobic monoalkyl glycol having a structure of formula I:

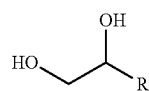

formula 1 wherein R=C4-C14 branched or unbranched alkyl group or alkylene group.

3. The poloxamer gel composition of claim 2, wherein the hydrophobic monoalkyl glycol is selected from the group consisting of 1,2-hexanediol, 1,2-octanediol, 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, and combinations thereof.

4. The poloxamer gel composition of claim 1, wherein the hydrophobic vicinal diol component comprises a hydrophobic monoalkyl glycerol having a structure of formula 2:

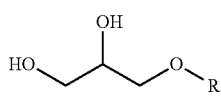

formula 2 wherein R=$C_6$-$C_{16}$ branched or unbranched alkyl group or alkylene group.

5. The poloxamer gel composition of claim 4, wherein the hydrophobic monoalkyl glycol is selected from the group consisting of glycerol 1-hexyl ether, glycerol 1-heptyl ether, glycerol 1-octyl ether, glycerol 1-(2-ethylhexyl)ether (also known as octoxyglycerin, 2-ethylhexyl glycerin, and 3-(2-ethylhexyloxy)propane-1,2-diol), glycerol 1-nonyl ether, glycerol 1-decyl ether, glyceryl 1-undecyl ether, glycerol 1-dodecyl ether, glycerol 1-tridecyl ether, glycerol 1-tetradecyl ether, glycerol 1-pentadecyl ether, and glycerol 1-hexadecyl ether, and combinations thereof.

6. The poloxamer gel composition of claim 1, wherein the hydrophobic vicinal diol component is a combination of 6-carbon to 16-carbon length monoalkyl glycols and 6-carbon to 16-carbon length monoalkyl glycerols.

7. The poloxamer gel composition of claim 1, wherein the composition is an aqueous poloxamer gel composition.

8. The poloxamer gel composition of claim 7, wherein the hydrophobic vicinal diol component depresses a sol-gel temperature of the aqueous poloxamer gel composition by at least 3° C.

9. The poloxamer gel composition of claim 8, wherein the sol-gel temperature of the aqueous poloxamer gel composition is at least 26.5° C.

10. The poloxamer gel composition of claim 1, wherein the aqueous poloxamer gel composition further comprises a solubilized or suspended silver salt, silver nanoparticle, zinc nanoparticle, zinc salt, calcium salt, gold salt, gold nanoparticle, magnesium nanoparticle salt, titanium nanoparticle salt, phosphorous compound, siloxy compound, iodine compound, barium salt, cerium compound, cobalt compound, copper compound, iron compound, manganese compound, nickel compound, strontium compound, or combination thereof.

11. The poloxamer gel composition of claim 1, wherein the poloxamer gel composition further comprises a biologically active agent, solubilized or suspended, the biologically active agent being an antibiotic, antimicrobial agent, antifungal agent, antiviral agent, antibacterial agent, anti-acne agent, anti-allergenic, psoriasis agent, analgesic, anesthetic, anticlotting agent, antihistamine, anti-protozoan agent, anti-parasitic agent, anti-pruritic agent, arthritis agent, astringent, anorectal, anti-inflammatory agent, antimitotic, antiperspirant, chelating agent, deodorant, essential oil, eczema agent, antiseborrheic agent, cancer treatment agent, canker sore treatment agent, cold sore treatment agent, corticosteroid, cytokine, dental agent, depigmenting agent, diaper rash treatment agent, endocrine hormone, enzyme, glycolipid, immunological response modifier, keratolytic agent, joint pain agent, hair growth stimulant, heat shock protein, glycoprotein, growth factor, growth hormone, hemostatic, lipid, moisturizer, nasal active, non-steroidal anti-inflammatory drug (NSAID), protein, peptide, pediculicide, periodontal treatment agent, nucleic acid, protease inhibitor, photosensitizing active, polysaccharide, retinoid, rosacea agent, skin protectant/barrier agent, skin treatment agent, saccharide, scabicide, steroid, sunburn treatment agent, sunscreen, thermal and radiation burn treatment agent, transdermal active, vaginal active, vasoconstrictor, vasodilator, vitamin, wart treatment agent, wart removal agent, wound debriding agent, wound treatment agent, wound healing agent, wound antimicrobial agent, or combination thereof.

12. The poloxamer gel composition of claim 1, wherein the water-soluble polymer is selected from the group consisting of aloe vera, methylcellulose, hydroxyethylcellulose, hydroxypropylcellulose, hydroxypropylmethylcellulose, carboxymethylcellulose, polyquaternium-1, polyquaternium-6, polyquaternium-10, guar, hydroxypropylguar, hydroxypropylmethylguar, cationic guar, carboxymethylguar, maltodextrin, hydroxymethylchitosan, hydroxypropylchitosan, carboxymethylchitosan, N-[(2-hydroxy-3-trimethylammonium)propyl]chitosan chloride, water-soluble chitosan, hyaluronic acid and its salts, chondroitin sulfate, heparin, dermatan sulfate, amylose, amylopectin, pectin, locust bean gum, alginate, dextran, carrageenan, xanthan gum, gellan gum, scleroglucan, schizophyllan, gum arabic, gum ghatti, gum karaya, gum tragacanth, pectins, starch, tamarind gum, poly(vinyl alcohol), poly(ethylene oxide), poly(ethylene glycol), poly(methyl vinyl ether), polyacrylamide, poly(N,N-dimethylacrylamide), poly(N-vinylacetamide), poly(N-vinylformamide), poly(2-hydroxyethyl methacrylate), poly(glyceryl methacrylate), poly(N-vinylpyrrolidone), poly(dimethylaminoethyl methacrylate), poly(dimethylaminopropyl acrylamide), polyvinylamine, poly(diallyldimethyammonium chloride), poly(N-isopropylacrylamide), poly(N-vinylcaprolactam), and combinations thereof, provided that gel formation is maintained.

13. The poloxamer gel composition of claim 1, wherein the poloxamer gel composition further comprises an antimicrobial agent, the antimicrobial agent being a chlorhexidine salt, alexidine salt, poly(hexamethylenebiguanide) salt, benzalkonium salt, benzethonium salt, cetyltrimethylammonium salt, cetylpyridinium salt, didodecyldimethylammonium salt, N-heptyl-N-dodecylpiperidinium bromide, N-hexyl-N-dodecylpiperidinium bromide, glyceryl monolaurate, sorbic acid, or combinations thereof.

14. A method of lowering the sol-gel temperature of an aqueous poloxamer gel composition by at least 3° C., comprising:
adding 0.1 to 1.8 wt. % of a hydrophobic vicinal diol component to the aqueous poloxamer gel composition,
wherein the poloxamer gel composition comprises 17 to 46 wt. % of a poloxamer component,
wherein the poloxamer component is selected from the group consisting of Poloxamer 407, Poloxamer 188, and a combination thereof, and
wherein the hydrophobic vicinal diol component comprises monoalkyl glycols, monoalkyl glycerols, or a combination thereof.

15. The method according to claim 14, wherein the hydrophobic monoalkyl glycols and the monoalkyl group of the monoalkyl glycerols comprise between 6 to 16 carbon atoms in length; and wherein the hydrophobic substituents are aliphatic, linear or branched, and saturated or unsaturated.

16. The method according to claim 14, wherein the hydrophobic vicinal diol component comprises a hydrophobic monoalkyl glycol having a structure of formula 1:

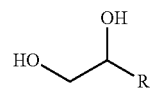

formula 1 wherein R=$C_6$-$C_{16}$ branched or unbranched alkyl group or alkylene group.

17. The method according to claim 14, wherein the hydrophobic vicinal diol component comprises a hydrophobic monoalkyl glycerol having a structure of formula 2:

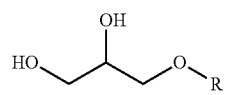

formula 2 wherein R=$C_6$-$C_{16}$ branched or unbranched alkyl group or alkylene group.

18. The poloxamer gel composition according to claim 1, wherein the poloxamer gel composition further comprises an active ingredient selected from the group consisting of at least 0.4% EDTA, at least 0.4% guar, at least 2% avobenzene, at least 2.5% lidocaine, 0.1% to 1% PHMB, at least 10% zinc oxide, at least 1% miconazole nitrate, at least 0.4% terbinafine, at least 0.5% acetylsalicylic acid, at least 5% *Leptospermum* Honey, at least 0.5% silver sulfadiazine, at least 0.5% amylase, and combinations thereof.

* * * * *